(12) United States Patent
Sato et al.

(10) Patent No.: US 7,695,462 B2
(45) Date of Patent: Apr. 13, 2010

(54) INDIVIDUALLY PACKAGED ABSORBENT ARTICLE

(75) Inventors: Nobuya Sato, Tochigi (JP); Kimiko Isobe, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/298,692

(22) Filed: Dec. 12, 2005

(65) Prior Publication Data

US 2006/0149201 A1    Jul. 6, 2006

(30) Foreign Application Priority Data

Dec. 15, 2004    (JP)    ............................. 2004-363717

(51) Int. Cl.
A61F 13/15    (2006.01)
A61F 13/20    (2006.01)

(52) U.S. Cl. ............................. 604/385.02; 604/385.04

(58) Field of Classification Search ............ 604/385.02, 604/385.28

See application file for complete search history.

(56) References Cited

U.S. PATENT DOCUMENTS

2003/0069556 A1 *    4/2003    Costa .................... 604/385.02

FOREIGN PATENT DOCUMENTS

| JP | 5-506799 A | 10/1993 |
|----|----|----|
| JP | 2002-272786 A | 9/2002 |
| JP | 2003-284741 A | 10/2003 |
| JP | 2003-290277 A | 10/2003 |
| JP | 2003284741 A | * 10/2003 |

OTHER PUBLICATIONS

English translation of JP 2003284741 A.*

* cited by examiner

*Primary Examiner*—Melanie J Hand
(74) *Attorney, Agent, or Firm*—Birch, Stewart, Kolasch & Birch, LLP.

(57)    ABSTRACT

An individually package structure 10 having an absorbent article 1 folded and packaged in a wrapper, the absorbent article 1 having an absorbent body 5 and a pair of flaps 6 extending laterally outward from the longitudinal side edges of the absorbent body 5. The absorbent body 5 has a skin facing side, a garment facing side, and an absorbent core between the skin facing side and the garment facing side. In the package, the absorbent article 1 has the flaps 5 folded over the skin facing side along respective fold lines LF and has an embossed pattern of depressions 62 formed on and/or near the fold lines.

10 Claims, 10 Drawing Sheets

INDIVIDUALLY PACKAGED ABSORBENT ARTICLE

FIELD OF THE INVENTION

The present invention relates to a package structure of individually packaged absorbent articles such as sanitary napkins, panty liners, incontinence pads, and disposable diapers.

BACKGROUND OF THE INVENTION

Absorbent articles with wings or flaps are known. JP-T-5-506799 discloses a sanitary napkin having flaps, which extend outwardly from the longitudinal side margins, folded over the topsheet. This arrangement maintains the topsheet in a sanitary condition and is more convenient to handle. The flaps may be maintained in this folded arrangement by a unitary release strip which bridges the flaps and covers any adhesive used to attach the flaps to an undergarment.

However, when the flaps are opened on use, a wrinkle remains near the fold lines to impair the feel or fit, which can result in leakage.

JP-A-2002-272786 discloses an absorbent article having a pair of wings each formed of a side nonwoven fabric which is fixed to the liquid impermeable backsheet by a linear heat seal along the longitudinal direction. The wings are heat embossed over the area except the base to improve the fixation of the adhesive thereon.

JP-A-2003-284741 discloses an absorbent article with flaps having embossed depressions for stopping liquid flow on their skin facing side. The back side of the flaps has no depressions and thereby provides a sufficient contact area to which an adhesive is applied. As a result, the adhesive is prevented from remaining on an undergarment when the napkin is removed.

JP-A-2003-290277 discloses an absorbent article having flaps that are not to be folded over the outer side of an undergarment. The flaps have depressions for stopping liquid flow on their skin facing side.

These techniques aim to stop liquid flow or to improve fixation of the adhesive onto the side flaps.

There is no related art proposing any structure that involves folding flaps inward (to face the topsheet) without creating folding wrinkles.

SUMMARY OF THE INVENTION

The present invention provides an individual package structure having an absorbent article folded and packaged in a wrapper. The absorbent article has an absorbent body and a pair of flaps extending outward from the longitudinal sides of the absorbent body. The absorbent body has a skin facing side, a garment facing side, and an absorbent core between the skin facing side and the garment facing side. The absorbent article has the flaps folded over the skin facing side thereof along respective two first fold lines and is folded along at least one second fold line perpendicular to the longitudinal direction of the absorbent body. The absorbent article has an embossed pattern on and/or near the first fold lines.

The package structure of the present invention is advantageous in that, when the absorbent article is taken out of the package and unfolded, the flaps and their vicinities hardly suffer from wrinkles. Therefore, impairment of feel is minimized, and the fit of the absorbent article to the body is secured to prevent leakage.

BRIEF DESCRIPTION OF THE DRAWINGS

FIG. 6 represents another embodiment of the present invention, in which

FIG. 8 represents still another embodiment of the present invention, in which

DETAILED DESCRIPTION OF THE INVENTION

The present invention will be described in detail with reference to the accompanying drawings.

Figure 1:
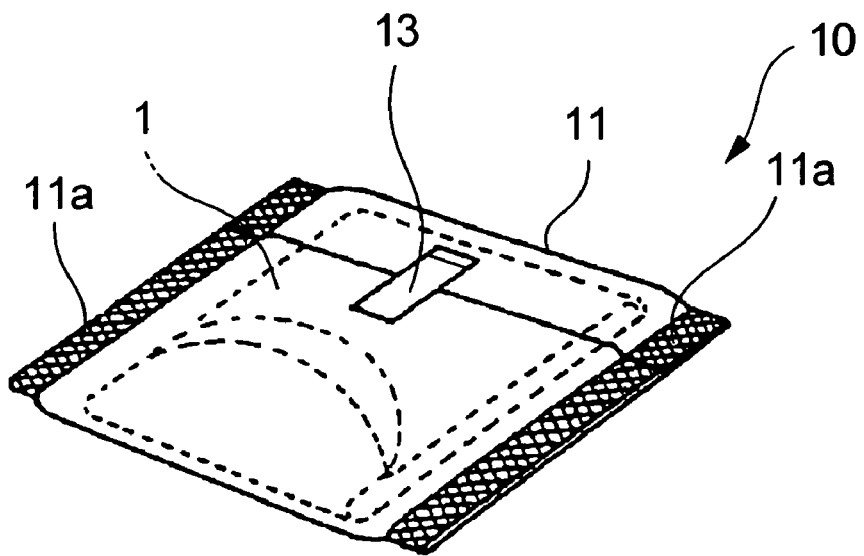
FIG. 1 is a perspective view of an embodiment of an individually packaged absorbent article according to the present invention, in which a sanitary napkin is packaged in a wrapper.

In a first embodiment of the present invention, an individually packaged sanitary napkin is provided, in which a sanitary napkin 1 is packaged in a wrapper 11 as illustrated in FIG. 1. In FIG. 1, numeral 10 indicates a package.

Figure 2:
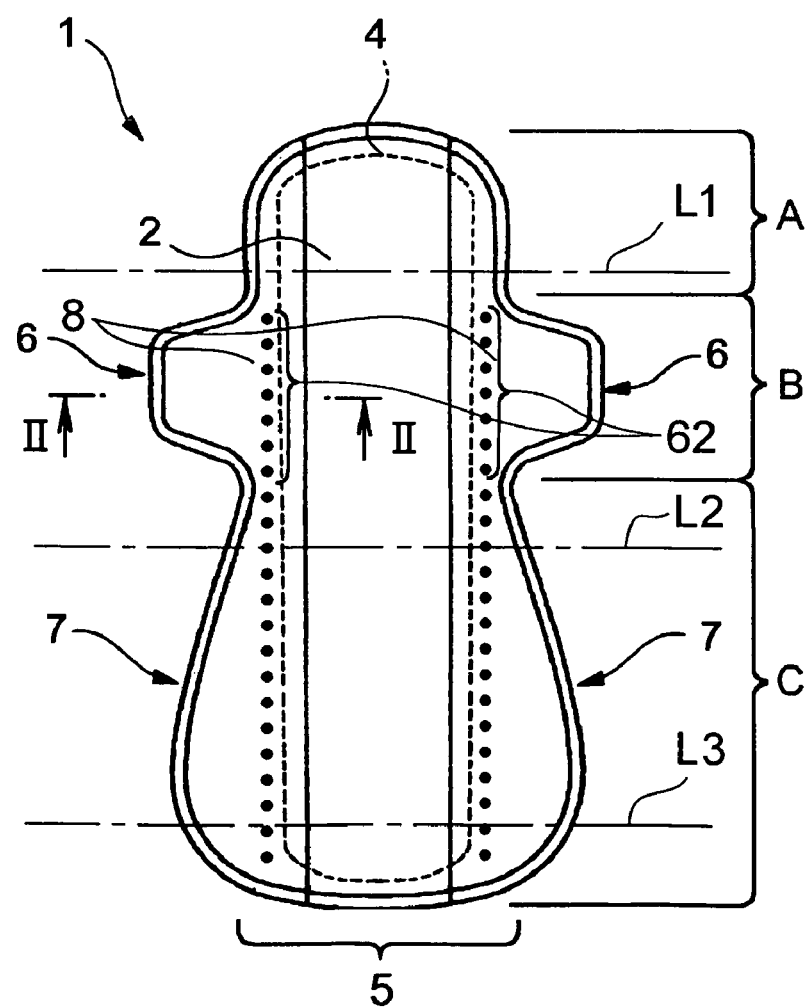
FIG. 2 is a plan view of the sanitary napkin in the package of FIG. 1 in its unfolded state, seen from the topsheet side thereof.
Figure 3:
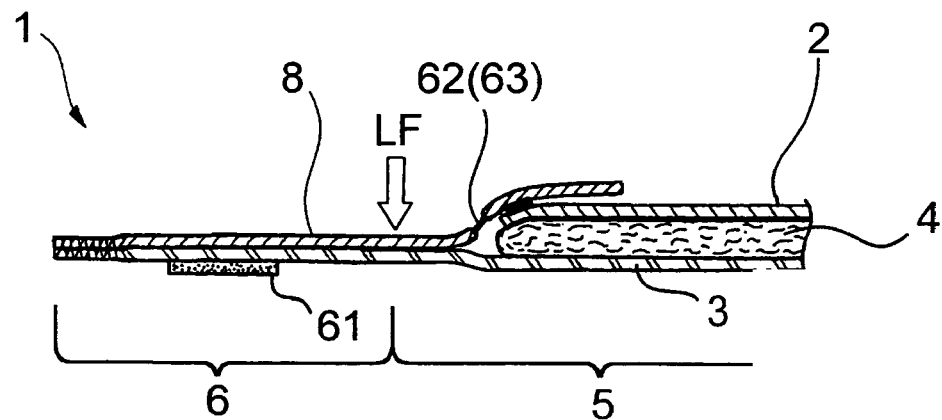
FIG. 3 is a fragmentary cross-sectional view of the sanitary napkin of FIG. 2 taken along line II-II in FIG. 2.

As illustrated in FIGS. 1 through 3, the sanitary napkin 1 has an absorbent body 5. The absorbent body 5 is substantially oblong rectangular and composed of a liquid permeable topsheet 2 that provides a skin facing side, a liquid impermeable backsheet 3 that provides a garment facing side, and an absorbent core 4 interposed between the topsheet 2 and the backsheet 3. The topsheet 2 covers the entire area of the upper side (skin facing side) of the absorbent core 4 and extends slightly outward from the longitudinal sides of the absorbent core 4 but is not in contact with the backsheet 3. The backsheet 3 covers the entire area of the lower side (garment facing side) of the absorbent core 4 and extends outward from the longitudinal sides of the absorbent core 4.

The sanitary napkin 1 has two pairs of flaps 6 and 7 extending outward form the longitudinal sides of the absorbent body 5. As illustrated in FIG. 3, the pair of flaps 6 is formed of a pair of water repellent side sheets 8 overlapping with the longitudinal side portions of the topsheet 2 and the side extensions of the backsheet 3. The pair of flaps 7 is also formed of the pair of side sheets 8 and the side extensions of the backsheet 3.

The sanitary napkin 1 is sectioned into a front portion A, a target portion B where a body fluid will be discharge, and a rear portion C. The flaps 6 located on both sides of the target portion B, which will be sometimes referred to as central flaps, should have a width enough to be draped over the edges of an undergarment and folded back and attached to the outer side of the undergarment.

An adhesive attachment layer 61 for attaching the napkin 1 to an undergarment is provided on the garment facing side of the absorbent body 5 and the flaps 6 and 7 (the adhesive attachment layer on the absorbent body 5 is not shown). On use, the sanitary napkin 1 taken out of the package 10 is unfolded and fixed on the inner side of an undergarment via the adhesive attachment layer of the absorbent body 5, and the flaps 6 are folded back under the undergarment and attached to the outer side of the undergarment via the adhesive attachment layer 61.

Figure 4A:
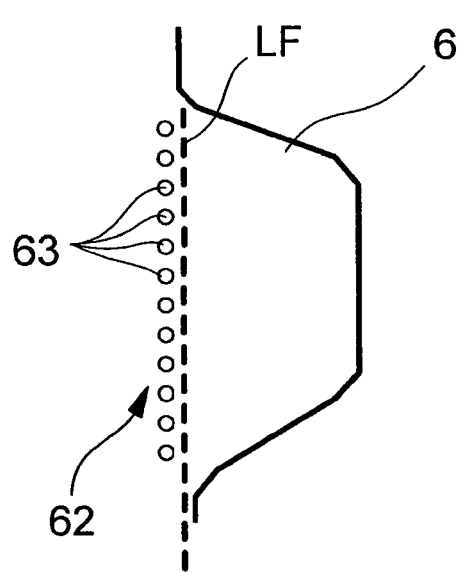
FIG. 4A is a plan view of a flap provided by the side of a target zone of the sanitary napkin of FIG. 2, showing a fold line and an embossed pattern near the fold line.
Figure 4B:
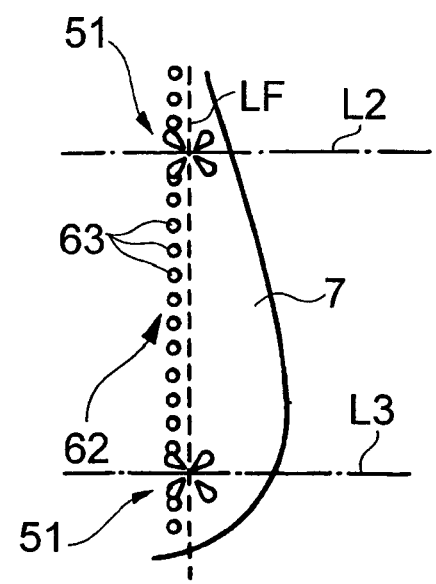
FIG. 4B is a plan view of a flap provided by the side of a rear portion of the sanitary napkin of FIG. 2, showing a fold line and an embossed pattern near the fold line.

As shown in FIGS. 3, 4A, and 4B, the sanitary napkin 1 has an embossed pattern 62 along both the longitudinal side edges of the absorbent body 5 where the base of each flap extends. In the first embodiment of the invention, the embossed pattern 62 is an array of discrete depressions 63 (pattern units) aligned substantially parallel to a fold line LF of the flap 6.

Figure 5A:
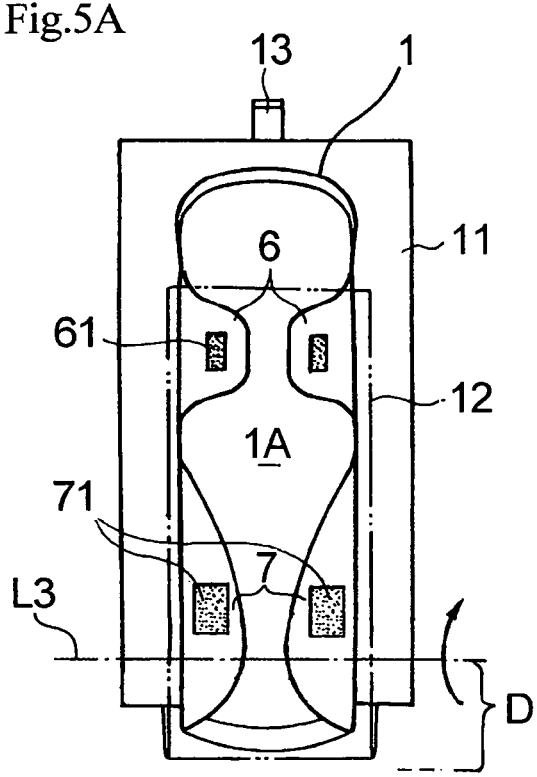
FIG. 5A and FIG. 5B each illustrate the way of folding the sanitary napkin to be packaged into the individual package of FIG. 1.

The individual package 10 of the sanitary napkin 1 is obtained as follows. As illustrated in FIG. 5A, the napkin 1 is placed on a wrapper 11 of sheet form with the flaps 6 and 7 folded over the topsheet side (skin facing side) of the absorbent body 5 along the longitudinal side edges of the absorbent body 5. The fold line LF of each flap 6 is in or near the area having the embossed pattern 62. The napkin 1 and the wrapper 11 are folded as a unit, with the skin facing side inside, along three longitudinally spaced apart and laterally extending fold lines L1, L2, and L3. In this state, the folded wrapper sheet 11 has edges laterally outward of the perimeter of the folded napkin 1. As shown in FIG. 1, the edges 11a of the wrapper 11 are sealed in a known manner, for example, by embossing, and the free end of the wrapper sheet 11 is fastened with a removable adhesive tab 13. The adhesive attachment layer 61 on the back side of the flaps 6 and 7 (the adhesive attachment layer on the back side of the absorbent body 5 is not shown in figures) is covered with a separately prepared release sheet 12 which is indicated by a double dashed chain line. The release sheet 12 is bonded to the wrapper sheet 11 via an adhesive 14.

As described, the sanitary napkin 1 of the present embodiment has a central pair of flaps 6 on both sides of the target portion B and a pair of flaps 7 on both sides of the rear portion C (hereinafter sometimes called "rear flaps"). All these flaps are folded onto the skin facing side of the absorbent body 5 along the respective fold lines located in a boundary region between the flap and the absorbent body 5.

Figure 5B:
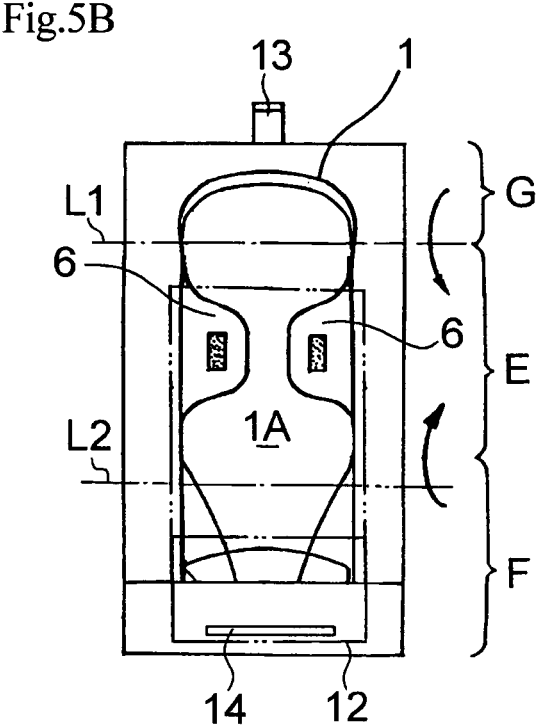
Figure 5C:
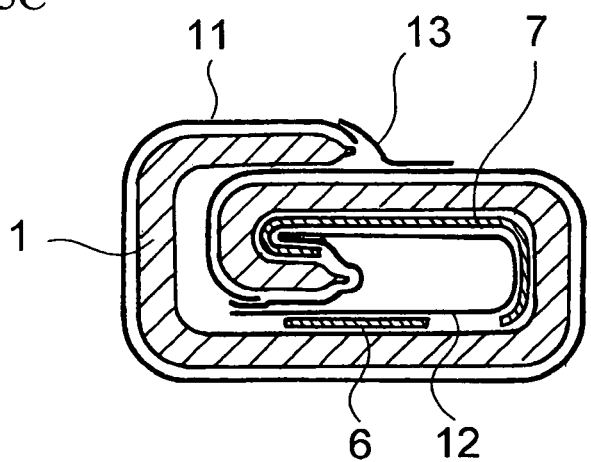
FIG. 5C is a side view of the packaged sanitary napkin of FIG. 1, seen through the wrapper.

In the package 10, the rear flaps 7 are folded over the skin facing side of the absorbent body 5 along the longitudinally extending fold lines LF and then folded along a fold line perpendicular to the longitudinal direction of the absorbent body 5 as shown in FIGS. 5A, 5B, and 5C. As shown in FIG. 4B, each fold line LF intersects with the laterally extending fold lines L3 and L2 in the rear flaps 7. In such a package, strong wrinkles occur easily around the intersections of the fold lines. In order to disperse the wrinkle-forming stress to prevent formation of a large wrinkle, it is preferred to arrange an embossed pattern containing a component in the direction of each of the intersecting fold lines around the intersections as illustrated in FIG. 4B. Other preferred examples of the embossed pattern that can be formed around an intersection of fold lines are shown in FIGS. 14A through 14D. The patterns 51a through 51d shown in FIGS. 14A to 14D each contain a component in the directions of the intersecting fold lines LF and L2 (or L3). FIG. 5C is a side view of the sanitary napkin 1 folded and packaged in the wrapper 11 seen through the wrapper 11.

In the first embodiment, the flaps 6 are folded about the respective fold lines LF positioned in the boundary region between each flap 6 and the absorbent body 5, and the absorbent body 5 is folded about fold lines crossing with the longitudinal direction of the absorbent body 5 at right angles in front and the rear of the flaps 6. That is, there are many folds near the flaps 6. Although folding an absorbent article many times makes it compact and convenient to carry, it induces as many folding wrinkles particularly around the central flaps provided near the target zone of the absorbent article.

In the present embodiment, the embossed pattern 62 (made up of discrete depressions 63) is formed along the absorbent core side of the longitudinal fold line LF so that a wrinkle generated near the fold line of the flap 6 may be deconcentrated and prevented from growing. As a result, the flaps 6 hardly create large wrinkles when folded and leave no large wrinkles when unfolded, and a folding wrinkle generated from near the fold line of the flaps is prevented from propagating to the target zone and causing a poor fit to the wearer's body, which can cause side leakage. Moreover, the sanitary napkin 1 maintains an agreeable feel to the touch.

Figure 6A:
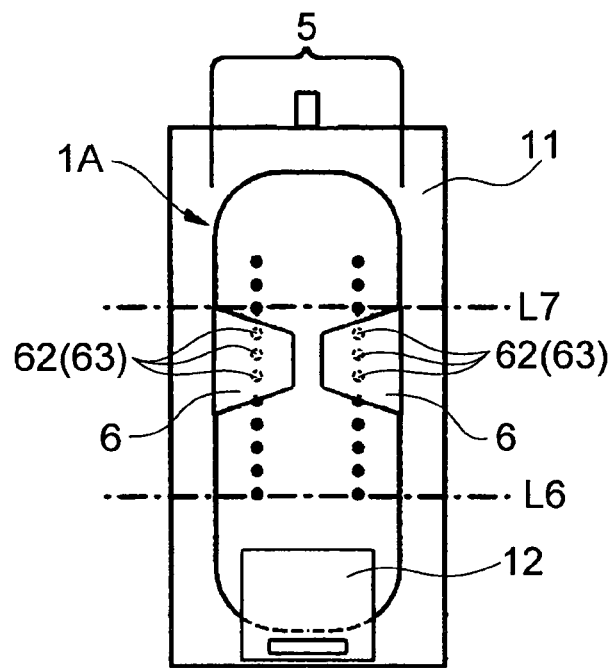
FIG. 6A illustrates the way of folding a sanitary napkin.
Figure 6B:
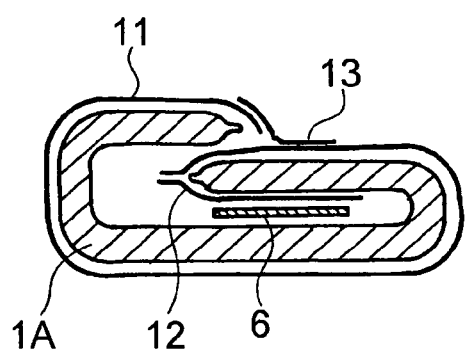
FIG. 6B is a side view of the folded sanitary napkin, seen through the wrapper.

Another embodiment (A second embodiment) of the individually packaged absorbent article according to the present invention is illustrated in FIGS. 6A and 6B, in which a sanitary napkin 1A is folded and packaged in the wrapper 11. The sanitary napkin 1A has a pair of flaps 6 on both sides of the target portion but does not have flaps in the rear portion. The wrapper 11 is formed of a sheet having release finish. A release sheet 12, which covers the adhesive attachment layer on the inward folded flaps 6, is fixed on its reverse side to the inner side of one end of the wrapper 11. The flaps 6 are each formed of a laterally outward extension of a side sheet extending over almost the whole length of, along the longitudinal side portion of, and on the skin facing side of, the sanitary napkin 1A. Each flap 6 is folded over the skin facing side of the napkin 1A to overlap the embossed pattern 62 (the depressions 63) formed on the side sheet.

The package of FIG. 6B is obtained by first folding the flaps 6 as illustrated in FIG. 6A, then folding the rear portion of the napkin 1A along a fold line L6 onto the middle part of the skin facing side of the napkin 1A, and finally folding the front portion of the napkin 1A along a fold line L7 onto the middle part of the napkin 1A. The free end of the wrapper 11 is fastened to the underlying panel of the wrapper 11 with a removable adhesive tab 13.

In this second embodiment, too, each of the flaps is folded about the longitudinally extending fold line located in the boundary region between the flap 6 and the absorbent body 5, and the absorbent body 5 is then folded about a laterally extending fold lines perpendicular to the longitudinal direction of the absorbent body 5 in front and the rear of the flaps 6. That is, there are many folds around the flaps 6. Although folding an absorbent article many times makes it compact and convenient to carry, it induces as many folding wrinkles particularly around the flaps provided near the target zone of the absorbent article.

Hence, the embossed pattern 62 (made up of discrete depressions 63) is formed is along the absorbent core side of the longitudinal fold lines so that a wrinkle generated near the folds of the flaps 6 may be deconcentrated and prevented from growing. As a result, the flaps 6 hardly create large wrinkles when folded and leave no large wrinkles when unfolded. A folding wrinkle generated from near the fold lines of the flaps is prevented from propagating to the target zone and causing a poor fit to the wearer's body, which can cause side leakage. Moreover, the sanitary napkin 1 maintains an agreeable feel to the touch.

Other embodiments of the individually packaged absorbent article of the present invention will be described with reference to FIGS. 7 through 13, in which a sanitary napkin 1B, 1C, 1D, 1E or 1F is folded and packaged.

Figure 7A:
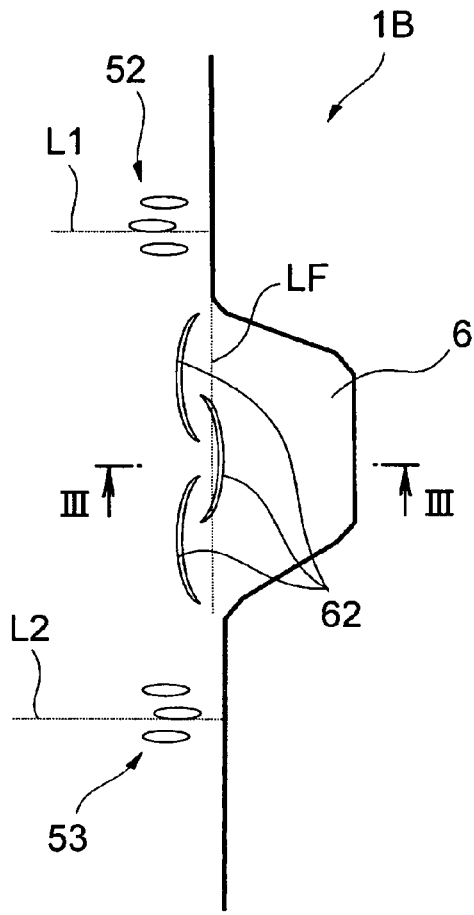
FIG. 7A and FIG. 7B each show a flap and its vicinity of a sanitary napkin according to still another embodiment of the present invention.
Figure 7B:
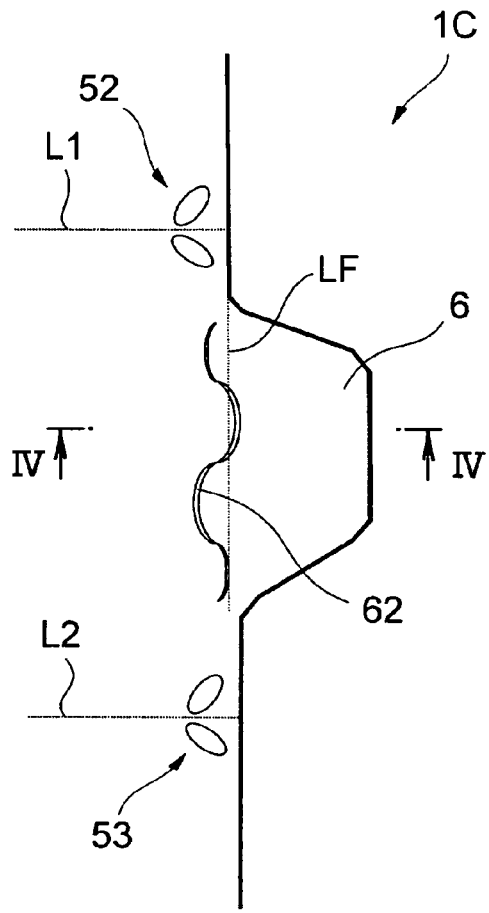
Figure 7C:
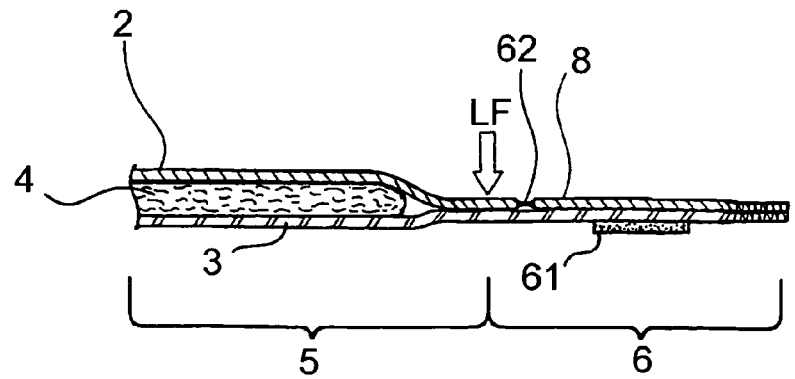
FIG. 7C is a cross-sectional view of FIGS. 7A and 7B taken along line III-III and line IV-IV.
Figure 8A:
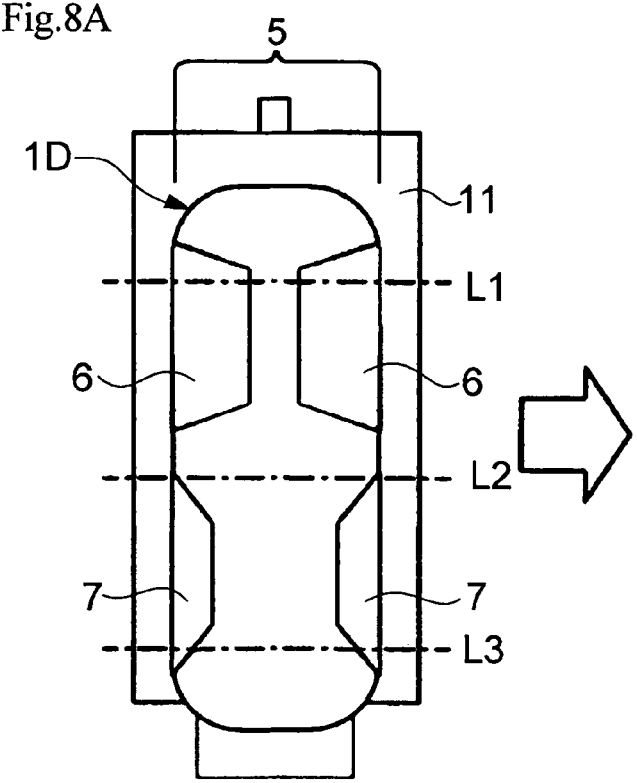
FIG. 8A and FIG. 8B illustrate the way of folding a sanitary napkin.
Figure 8B:
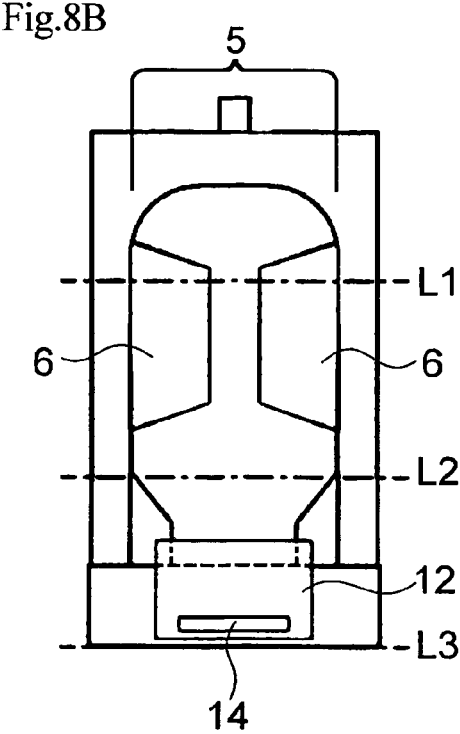
Figure 8C:
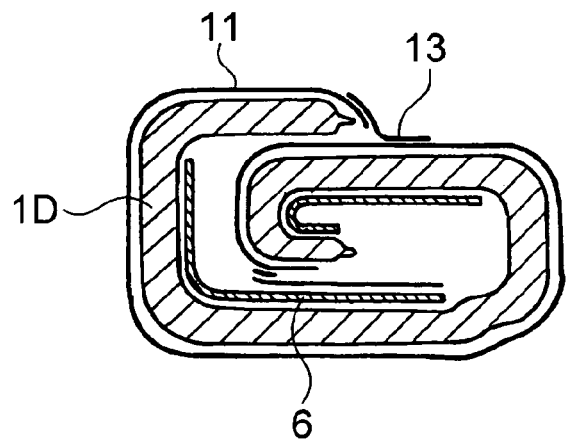
FIG. 8C is a cross-sectional view of the sanitary napkin thus folded, seen through the wrapper.

As illustrated in FIGS. 7A and 7B, the sanitary napkins 1B and 1C have embossed patterns 52 and 53 made along each longitudinal side portion of the absorbent body 5. The sanitary napkins 1B and 1C have a pair of flaps 6 formed of extensions of the topsheet 2 and the backsheet 3 from both longitudinal side edges of the absorbent body 5. In the package, the flaps 6 are folded over the skin facing side of the absorbent body 5 along the respective fold lines LF, and the absorbent article 1B or 1C and the wrapper 11 are folded as a unit in the longitudinal direction (i.e., along fold lines L1 and L2 perpendicular to the longitudinal direction of the absorbent body 5). An embossed pattern 62 is formed on and/or near each fold line LF, and embossed patterns 52 and 53 are formed on and/or near the fold lines L1 and L2, respectively. The embossed pattern 62 formed along the longitudinal fold line LF of the napkin 1B is made of discrete, arc-shaped depressions aligned in the longitudinal direction of the napkin 1B with alternating curving directions. In a side view of the napkin 1B, adjacent arc-shaped depressions overlap at their ends. The embossed pattern 62 formed along the longitudinal fold line LF of the napkin 1C is made of arc-shaped depressions connected in the longitudinal direction of the napkin 1C with their curving directions alternating.

In general, a thick absorbent body easily get wrinkles when folded. In the package structure of FIGS. 7A and 7B, the absorbent body 5 is prevented from developing a large wrinkle by forming an embossed pattern of depressions on and near the fold lines. Hard set wrinkles are caused by folding when an absorbent article has increased stiffness in its longitudinal side portions due to the presence of more constituent materials than in the other parts or due to the presence of joints between the constituent materials or when a wrinkle formed by folding is not allowed to escape because of the side closure. The package structure of the invention is particularly effective in such cases. That is, development of a wrinkle is dispersed by forming embossed depressions in the vicinity of the fold lines in at least the longitudinal side portions of the absorbent article. As a result, when the absorbent article is taken out of the package and unfolded, there is not left a large wrinkle, and the absorbent article provides a good fit to the wearer's groin.

Still another embodiment of the present invention is illustrated in FIGS. 8A, 8B, 8C, and 9, in which a sanitary napkin 1D is folded and packaged. The sanitary napkin 1D has a pair of central flaps 6 and a pair of rear flaps 7. The central flaps 6 are larger in the longitudinal direction of the napkin than those of the napkin 1 used in the first embodiment. On use, the rear flaps 7 are applied flat to the skin facing side of an undergarment. The flaps 6 and 7 are formed of a side sheet and a backsheet similarly to the napkin 1. An embossed pattern 62 is formed in the flaps 6 along the outward side of the longitudinal side edges of the absorbent body.

Figure 9:
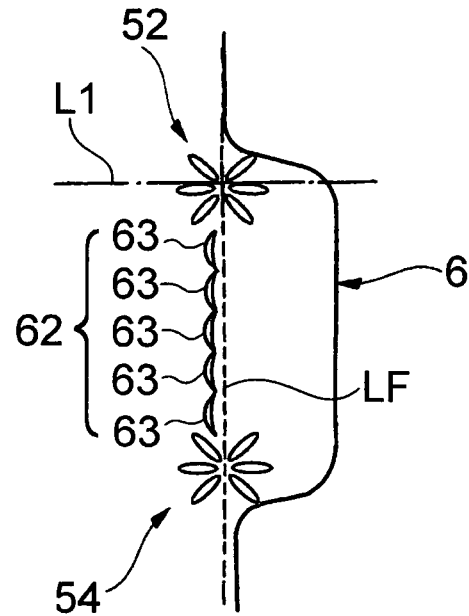
FIG. 9 is a plan view of a central flap of the sanitary napkin of FIGS. 8A, 8B and 8C, showing a fold line and an embossed pattern near the fold line.

In the package, the flaps 6 and 7 are folded over the topsheet side (skin facing side) of the absorbent body 5, and the napkin 1D with its flaps folded in is folded as a unit with a wrapper 11 of sheet form along fold lines perpendicular to the longitudinal direction of the absorbent body. As illustrated in FIG. 9, an embossed pattern 62 is formed on and/or near the fold line LF of each flap 6, and embossed patterns 52 is formed on and/or near the fold line L1 of the absorbent body 5. The pattern 52 is located on and around the intersection of the fold lines LF and L1. The pattern 54 is imparted for design reasons. Other constitutional details of this embodiment are the same as for the first and second embodiments.

In the embodiment of FIGS. 8 and 9, since each of the flaps 6 is folded along the longitudinal fold line positioned in the boundary region between the flap 6 and the absorbent body 5 and further folded about a fold line perpendicular to the longitudinal direction of the absorbent body 5, the napkin 1D suffers from notable, hard set wrinkles near the intersections of these fold lines. Even in such a configuration, wrinkles are allowed to disperse and thereby prevented from growing by forming an embossed pattern of depressions on and near the fold lines of the flaps. As a result, when the absorbent article is unfolded on use, there is left no large wrinkles, and the article gives a wearer comfort and provides a protection against side leakage caused by a reduced fit.

Referring back to FIG. 2, the sanitary napkin 1 has its central flaps 6 positioned between the fold lines L1 and L2 about which the absorbent body 5 is folded into three panels. The size of the flaps 6 in the longitudinal direction of the absorbent body can be increased to ensure protection against side leakage. Then, the longitudinal fold line of the flap 6 and the lateral fold line of the absorbent body may intersect with each other. The package structure of the present invention is especially effective in packaging such an absorbent article with a relatively wide flaps.

Figure 10:
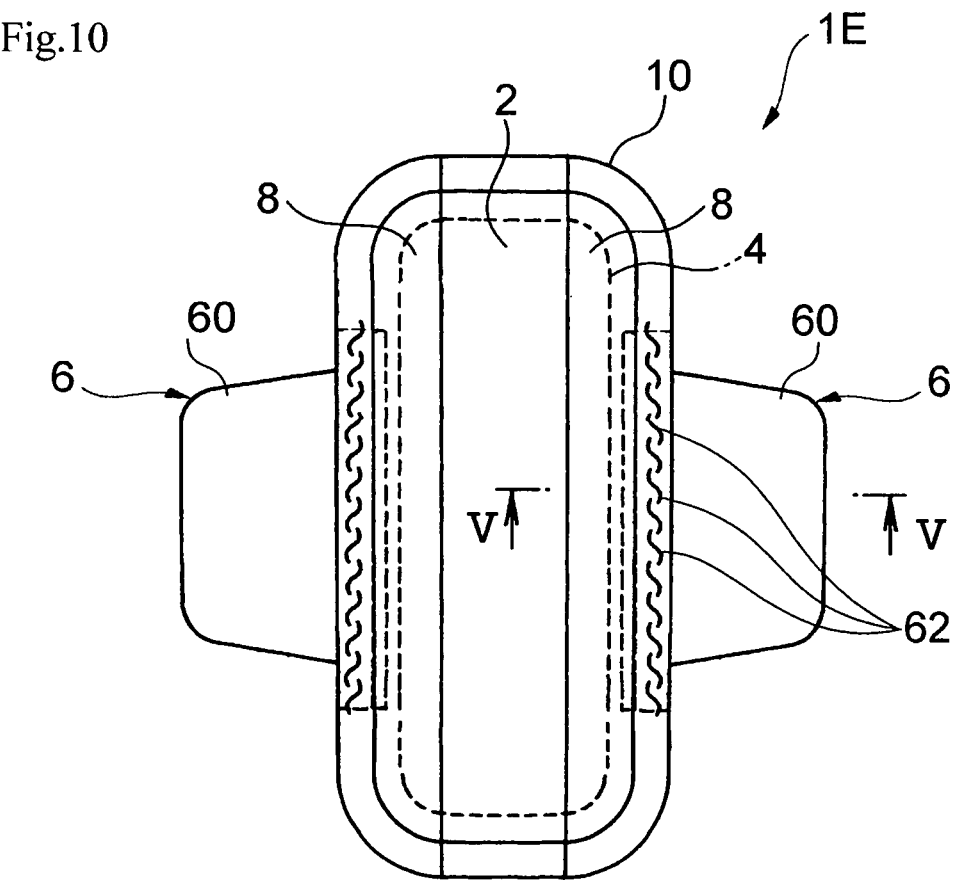
FIG. 10 is a plan view of still another embodiment of a sanitary napkin according to the present invention, seen from the topsheet side thereof.
Figure 11:
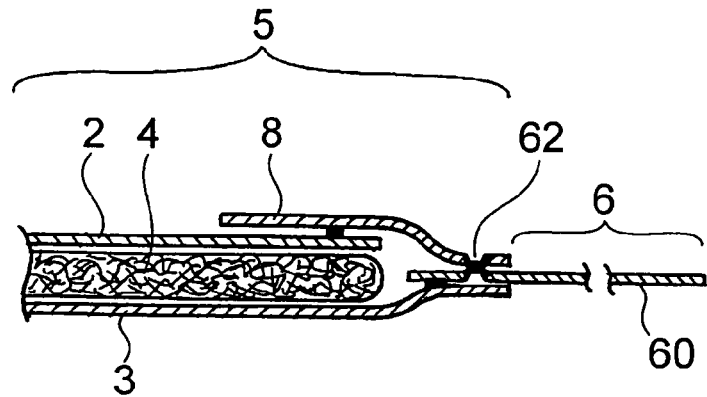
FIG. 11 is a fragmentary cross-sectional view of the sanitary napkin of FIG. 10, taken along line V-V in FIG. 10.

FIGS. 10 and 11 illustrate a sanitary napkin 1E used in yet another embodiment of the present invention. The napkin 1E has a pair of flaps 6 formed of flap-forming sheets. The flap-forming sheets are separate from both the topsheet 2 and the backsheet 3 and connected to the absorbent body 5. The napkin 1E also has a pair of side sheets 8 disposed on both longitudinal side portions of the skin facing side of the absorbent body 5. Each of the side sheets 8 and the backsheet 3 extend over the side edges of the absorbent body 5. The flap-forming sheet is joined with the backsheet 3 with an adhesive and with the side sheet 8 by heat sealing. The heat sealing between the side sheet 8 and the flap-forming sheet simultaneously forms an embossed pattern 62.

In addition to the heat sealing, other means such as an adhesive or ultrasonic embossing may be used to join the flap-forming sheet and the side sheet. The bonding of the flap-forming sheet and the backsheet is accomplished similarly.

The flap-forming sheet includes a nonwoven fabric sheet and a nonwoven fabric/resin film composite sheet. Useful nonwoven fabrics include those made of synthetic fibers of polyolefins, polyesters or polyamides having a thickness of 1 to 3 dtex by thermally bonding the fibers (thermal bonded nonwovens), bonding the fibers using an adhesive (chemical bonded nonwovens), or entangling the fibers by needle punching (needle punched nonwovens) or by water needling (hydroentangled nonwovens). Spun bonded nonwovens made of continuous fibers and melt blown nonwovens of the above resins and composites thereof are also useful. The nonwoven fabric may be made stretchable by using, as potential crimping fiber, conjugate fiber having a side-by-side configuration or an eccentric sheath-core configuration. Nonwoven fabric stretchable in the transverse direction obtained by stretching spun bonded nonwoven fabric made of continuous fibers in the machine direction may be used to provide improved fit. A laminate of the stretchable spun bonded nonwoven fabric or a hydroentangled (spunlaced) nonwoven fabric stretchable in the transverse direction and a thermoplastic elastomer film also provides an improved fit. The thermoplastic elastomer is selected as appropriate from styrene elastomers, olefin elastomers, urethane elastomers, and ester elastomers. The flap-forming sheet preferably has a weight of 30 to 100 g/m$^2$.

The absorbent article having the above-described structure have many constituent materials overlapping in the vicinities of the base of the flap, i.e., the flap-forming sheet, the topsheet, the side sheet, and the backsheet. Therefore, wrinkles develop easily on folding the flaps due to differences among these materials in physical properties such as tensile characteristics and stiffness. Even with such a configuration, the wrinkle developing around the fold line of the flap is dispersed and prevented from growing by making depressions around the fold line.

Where the topsheet has a large thickness, wrinkles easily grow due to bagginess when the flaps are folded over the skin facing side. Where, in particular, a bulky sheet is used as a topsheet to provide a pleasant feel, and a not-so-thick side sheet is bonded to the side portions of the absorbent body to ensure leakproofness, a folding wrinkle easily occurs because of the difference in thickness between the sheets. In cases where the topsheet is twice or more, particularly 5 times or more, especially 10 times or more, as thick as the side sheet, the folding wrinkle problem in packaging the absorbent article can be solved by forming an embossed pattern of depressions along the longitudinal sides of the skin facing side of the absorbent article, folding the flaps over the skin facing side of the absorbent body about a fold line which intersects with the curved embossed pattern and extends along the longitudinal direction of the absorbent article, and then folding the absorbent article about a fold line perpendicular to the longitudinal direction of the absorbent body.

Yet still another embodiment of the individually packaged absorbent article of the present invention will be described with reference to FIGS. 12, 13A, and 13B, in which a sanitary napkin 1F to be packaged is illustrated.

As shown, the sanitary napkin 1F has an absorbent body 5 and a pair of side sheets 8. The absorbent body 5 is composed of an absorbent pad D and a leakproof layer E. The side sheets 8 are provided on the longitudinal side portions of the skin facing side of the absorbent body 5 over substantially the whole length of the absorbent body 5. Each side sheet 8 is embossed to have a pattern of depressions along the fold line of each flap 6 (described later) in order to disperse folding wrinkles generated around the flaps 6. The pattern of depressions extends over substantially the whole length of the flap 6 in the longitudinal direction of the side sheet 8. The pattern of depressions contains, in its plan view, linear pattern units having a larger component in the fold line direction than in the direction perpendicular to the fold line.

Figure 12:
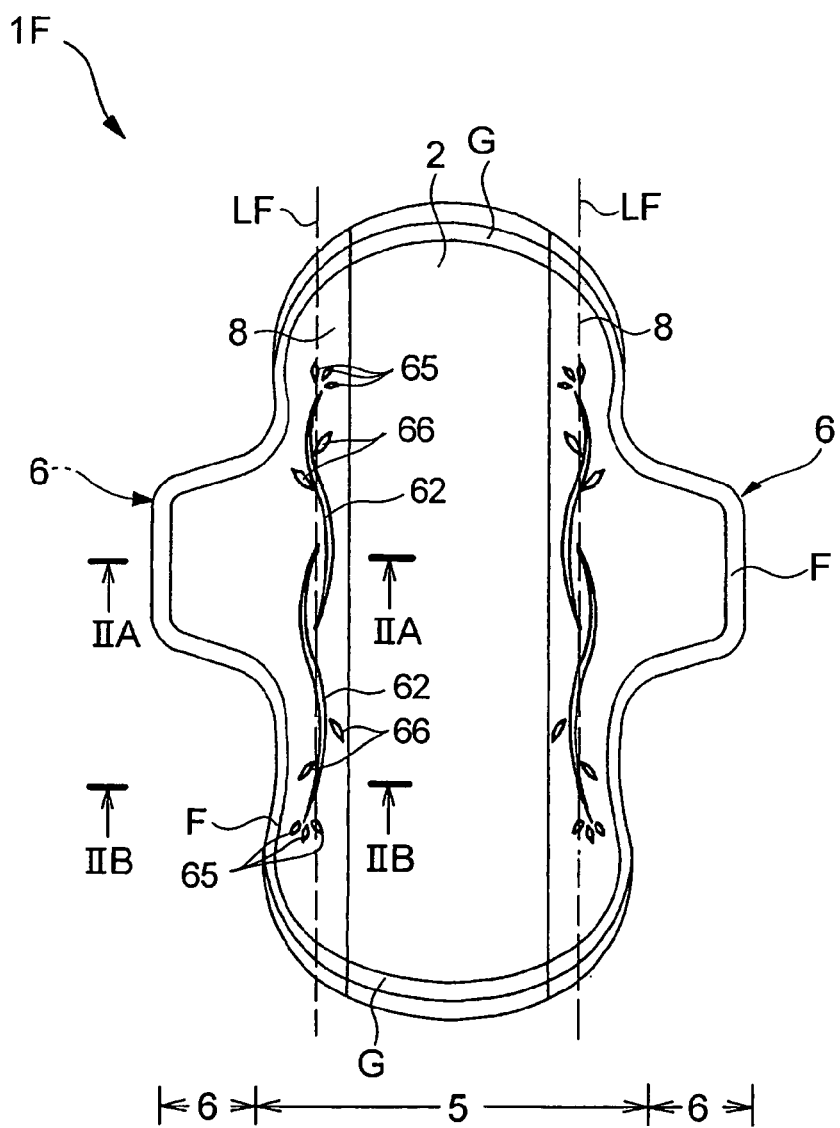
FIG. 12 is a plan view of yet another embodiment of a sanitary napkin according to the present invention, seen from the topsheet side thereof.

As illustrated in FIG. 12, a pair of the side sheets 8 are provided on the longitudinal side portions of the skin facing side of the absorbent body 5 over substantially the entire length of the absorbent body 5. A pair of flaps 6 are formed on both sides of the target zone of the absorbent body 5. As is seen from FIG. 13A, the flap 6 is made of the outboard extension of the backsheet 3 and the outboard extension 8C of the side sheet 8.

Figure 13A:
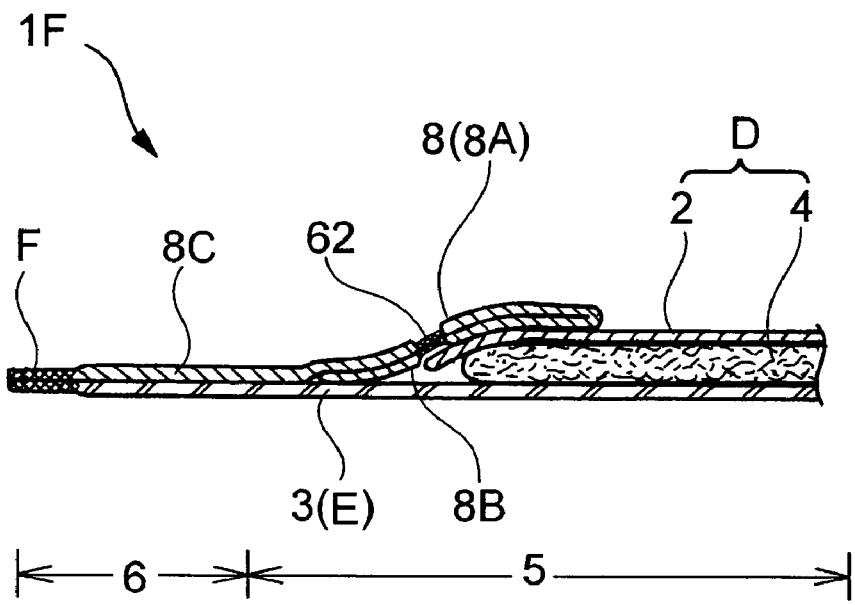
FIG. 13A is a cross-section taken along line IIA-IIA in FIG. 12.
Figure 13B:
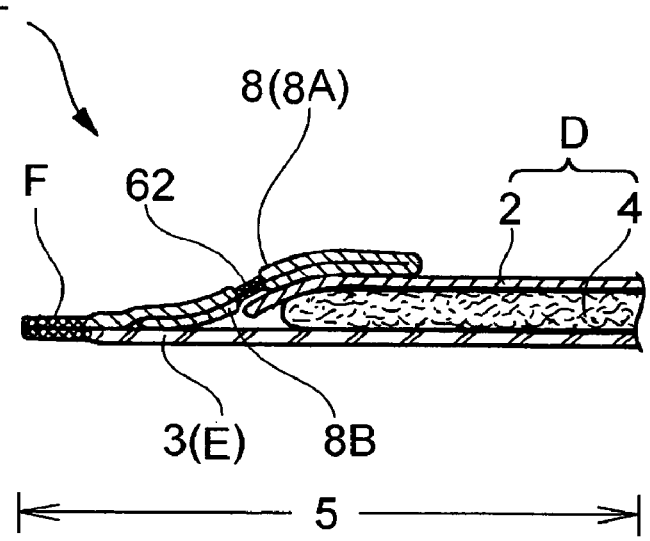
FIG. 13B is a cross-section taken along line IIB-IIB in FIG. 12.
Figure 14A:
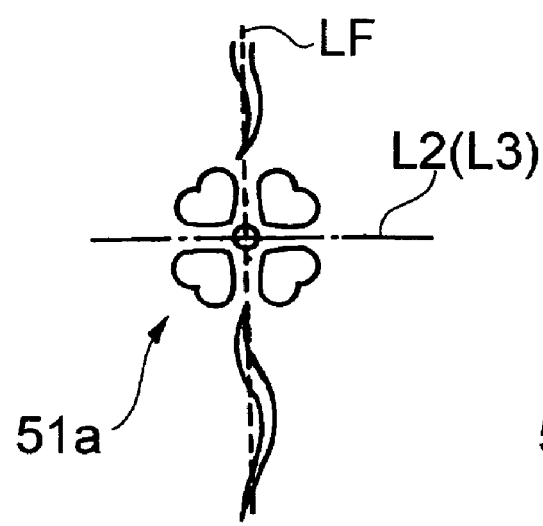
FIG. 14A, FIG. 14B, FIG. 14C, and FIG. 14D each show a preferred pattern of embossing given to the vicinities of an intersection of fold lines.
Figure 14B:
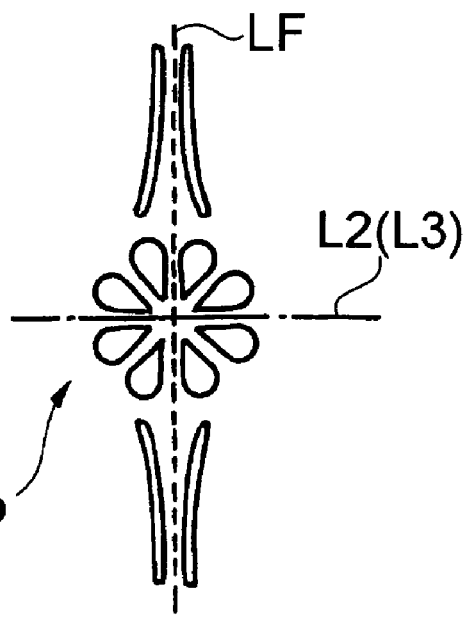
Figure 14C:
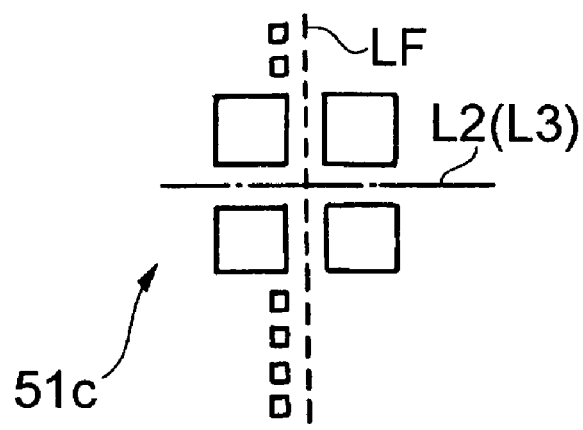
Figure 14D:
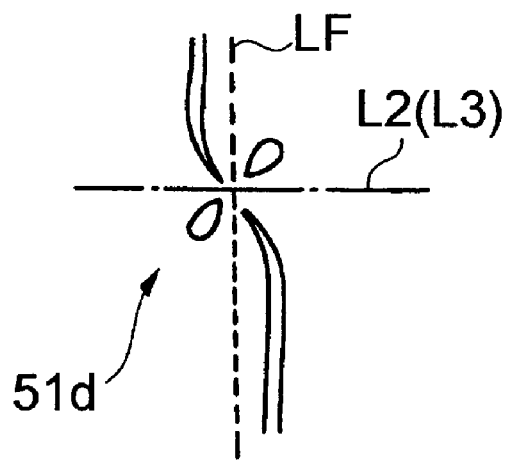

As illustrated in FIGS. 12, 13A, and 13B, the backsheet 3 and the side sheet 8 are joined together along the longitudinal side edges of the absorbent body 5 and along the periphery of the flaps 6 to form side seals F. The topsheet 2 and the backsheet 3 extend outward from the front and the rear ends of the absorbent core 4 and joined together in the extensions to form end seals G as illustrated in FIG. 12.

The backsheet 3 and each side sheet 8 are also joined together via an adhesive (not shown) near the longitudinal side edges of the absorbent body 5 and over the area of the flaps 6 as illustrated in FIGS. 13A and 13B. The side sheet 8 on the skin facing side of absorbent body 5 is folded back onto the topsheet 2 such that the folded edge is located above the absorbent core 4 and the loose, raw edge is in contact with the backsheet 3. An adhesive is applied to bond between the folded panels 8A and 8B of the side sheet 8, between the side sheet 8 and the backsheet 3, and between the side sheet 8 and the topsheet 2. The folded panels 8A and 8B are also joined to each other by patternwise sealing (embossing). The seal is formed by (1) embossing in a pattern composed of linear pattern units having a larger component in the fold line direction than in the direction perpendicular to the fold line, (2) embossing in a pattern (a combination of pattern units) along the fold line direction in a folded region, (3) embossing in a pattern composed of two or more pattern units that are arranged on the both sides of the fold line in a folded region, or (4) a combination of (1) to (3).

As illustrated in FIG. 12, an embossed pattern composed of depressions 62, 65, and 66 as pattern units is imparted to the side sheet 8. The individual pattern units (depressions) may be the same or different. In this particular embodiment of FIG. 12, the pattern consists of a few types of pattern units.

The term "linear pattern unit" as used with respect to the above-described first mode of embossing is intended to mean a pattern unit parallel with the fold line LF as a whole. The linear pattern unit does not always need to be parallel with the fold line LF in every microscopic detail in the plan view. For example, the two depressions 62 depicted in FIG. 12 cannot be said to be parallel to the fold line LF in its every detail but, when seen macroscopically, they extend along the fold line LF.

The "linear" pattern unit does not need to be straight linear. For example, a pattern unit may be a composite of two or more non-straight line segments, such as curved line segments. The phrase "having a larger component in the fold line direction than in the direction perpendicular to the fold line" means that a rectangular region circumscribed about a linear pattern unit composed of two or more curved line segments is longer in the fold line direction than is wide in the direction perpendicular to the fold line.

The expression "a pattern (a combination of pattern units) along the fold line direction" as used with respect to the above-described second mode of embossing means an array of discrete pattern units (depressions) aligned near the fold line LF to form a pattern substantially parallel to the fold line LF as a whole. FIG. 9 presents an example, in which a plurality of depressions 63 (pattern units) are aligned along the fold line LF to make the pattern 62 along the fold line LF. The pattern units (the shape of the depressions) making the pattern along the fold line may be the same or different in the plan view.

The pattern along the fold line can be composed of, for example, a plurality of pattern units having shapes with a rounded outline. For example, pattern units such as hollow circles, ellipses, heart shapes, and leaf shapes can be aligned along the fold line direction to give a good impression to a user as well as to exert the effect of dispersing wrinkle forming stress.

The expression "arranged on the both sides of the fold line" as used with respect to the above-described third mode of embossing means that at least two pattern units are discretely arranged on the both sides of the fold line like sandwiching the fold line, when viewed in a plan view. Examples of a pattern having such an arrangement are given in FIGS. 14A through 14D. In the patterns 51*a* to 51*d* shown in FIGS. 14A through 14D, four or eight pattern units arranged around the intersection of the fold line LF and the laterally extending fold line L2 (or L3) make up a pattern composed of two or more pattern units that are arranged on the both sides of the fold line LF.

By the third mode of embossing, the folding stress causing wrinkle development in the direction basically parallel to the fold lines can be diffused only to form fine wrinkles. In a preferred pattern according to the third mode of embossing, the facing pattern units on the both sides of the fold line have no parts parallel to each other. By this preferred pattern, the folding stress is prevented from forming a large ridge and is dispersed into small wrinkles. This type of pattern units is required to have a certain size, particularly in length in the fold line direction. Accordingly, a pattern unit with a small depressed area, such as a pattern unit having a hollow shape is preferred. The pattern of the third mode of embossing is suitably formed at or around an intersection of fold lines. Where a longitudinally extending fold line and a laterally extending fold line intersect with each other, pattern units can be arranged on the respective both sides of these two fold lines thereby to disperse the wrinkle-forming stress.

In addition to the above-described modes of embossing, the part of the flaps laterally outboard of the respective fold lines may be embossed to form depressions similar to those formed in the vicinities of the fold lines to reduce wrinkles that may develop in the flaps per se. For example, the pattern unit having the heart shape (51*a*), the drop shape (51*b* and 51*d*) or the square shape (51*c*) shown in FIGS. 14A to 14D may be arranged in the flaps in an arbitrary fashion. The pattern unit having the heart shape of FIG. 14A can be arranged in an appropriate manner in the part of each flap outboard of each fold line LF.

To prevent wrinkling, the embossed pattern to be formed in the part of each flap outboard of the fold line LF is preferably formed as an extension from the area where pattern units are arranged to make a pattern. For example, the above-mentioned pattern units facing across the fold line direction may be repeated in the laterally outward direction into the flaps, or a continuous pattern may be formed in the flaps like a lattice pattern. The lines forming the lattice pattern preferably have an angle, e.g., of 30° or less, from the longitudinal direction of the absorbent article, i.e., the fold line. Although the pattern may be extended to reach the outboard end of the flap, it suffices that the pattern extends up to the area where the flap is folded in packaging.

The topsheet that can be used in the present invention is not particularly limited. In the present embodiment, hydrophilic nonwoven fabric is used. The backsheet that can be used in the present invention is not particularly limited. In the present embodiment, a leakproof plastic film is used. The absorbent core used in the present invention is conventional. The side sheet is preferably a hydrophobic nonwoven fabric or a leakproof plastic sheet. In the present embodiment, a hydrophobic nonwoven fabric is used.

The wrapper that can be used in the present invention includes resin film (e.g., a polyethylene film) having a release surface or resin film to which a sheet of release paper is joined. A spun bonded nonwoven fabric sheet or a laminate sheet composed of nonwoven fabric and polyethylene film is also useful. These sheets may have silicone, etc. applied to the inner side thereof for releasability. The releaser sheet that can be used to cover the adhesive side of the flaps includes paper, resin film, nonwoven fabric, and nonwoven fabric laminated with resin film, each having been treated with silicone, etc.

Where nonwoven fabric is used as a wrapper for individually packaging an absorbent article, air easily escapes from the package when the article as folded and packaged is pressed under a roll, etc. It tends to follow that a considerable compressive force is imposed to the article to cause hard set folding wrinkles. The package structure according to the present invention is therefore particularly effective in preventing large and hard set wrinkles from being created where a highly air-permeable wrapping material such as nonwoven fabric is used as a wrapping material or where the wrapping material is air impermeable but has air escape holes through which air escapes easily when the absorbent article is compressed for sealing the wrapper.

The method of forming an embossed pattern of depressions is not particularly restricted. In the present embodiment, the embossed pattern of depressions is formed by heat embossing using a heated embossing roll. To impart a clearly embossed pattern while keeping the soft hand around the depressions, the embossing roll temperature is preferably 90° to 150° C., still preferably 110° to 130° C. At embossing temperatures lower than 90° C., embossing will be weak only to produce a small wrinkle dispersing effect. At temperatures higher than 150° C., the parts surrounding the depressions become hard.

In the embodiment of FIGS. 12, 13A, and 13B, the side sheet 8 is formed of a sheet of continuous length that has previously been folded back along one side edge to have the width as in a final product and embossed to have a pattern of depressions. The folded and embossed sheet of continuous length is joined to each side portion of the absorbent body 5 with an adhesive, cut and trimmed at both the front and the rear ends, and sealed to form the end seals G. The sanitary napkin 1F with an embossed pattern of depressions on its side sheets 8 is thus obtained easily.

The sanitary napkin 1F has a pattern of depressions formed on the side sheets 8 over the whole length of the flaps in the longitudinal direction of the absorbent body 5 so that a wrinkle developing on folding the flaps over the skin facing side may be dispersed. The embossed pattern of depressions prevents a wrinkle from generating on the side sheets 8 when the flaps 6 are folded over, prevents the nonwoven fabric (side sheets 8) from lifting due to bagginess, and stops propagation of the wrinkle if any. As a result, the side sheets 8 hardly develop a large wrinkle, and the flaps 6 can be folded with little wrinkling, and, after the flaps are unfolded, there is left no large wrinkle that could invite side leakage and reduce the hand.

Where a linear pattern unit having a large component in the fold line direction than in the direction perpendicular to the fold line has a gradually decreasing width toward the ends, the linear pattern unit is bent at the narrow parts, and the wide part hardly rises into a ridge. As a result, a raised part hardly buckles to form a wrinkle or a crease that will remain even after the flaps are unfolded.

The absorbent article of the present invention is not limited to those described above, and various changes and modifications can be made therein without departing from the spirit and scope of the present invention. The individual package structure according to the present invention is applicable to not only sanitary napkins as hereinabove described but panty liners, incontinence pads, and disposable diapers.

The embossed pattern may be a single linear depression extending the whole width (or sometimes referred to as "length") of the flaps in the longitudinal direction of the absorbent article or consist of a plurality of linear pattern units each having only one inflection point.

Examples of embossed patterns formed on both longitudinal side portions of the skin facing side of an absorbent article have been illustrated. The embossing is preferably done over a sufficient region with reference to the fold length of the flaps. Still preferably, the embossing is done over a length longer than the width of the flaps in the longitudinal direction of the absorbent article. With respect to the position of embossing in the transverse direction of the absorbent article, it is preferred that at least part of the embossed pattern be in the inboard side of the fold line (i.e., the flex axis) of the flap. By forming an embossed pattern inboard of the fold line, a ridge of a sheet material raised by the flap being folded over the skin facing side is prevented from progressing toward the skin contact surface of the absorbent article. As a result, folding wrinkles caused by the sheet material's becoming baggy on the skin facing side of the absorbent article can be reduced. Accordingly, in order that a folding wrinkle developing on folding the flap onto the skin facing side may be dispersed so as not to propagate to the target portion, the embossing is preferably done in a region between the outer edge of the target portion of the absorbent body and the fold line (i.e., the flex axis) of the flap. A folding wrinkle is particularly liable to occur in a region having many members overlapped (i.e., the longitudinal side edges of the absorbent core where the leakproof sheet, absorbent core, the topsheet, and the side sheet overlap) and about the boundary between that region and where the number of the constituent members drastically decreases. Then, by forming the embossed pattern over an area from the region with many members to the boundary slightly outboard of the region, lift of the sheet material due to embossing is prevented, a wrinkle is dispersed between embossed depressions so as not to grow, and a wrinkle is prevented from propagating in the lateral direction toward the target zone.

Where the absorbent body has an increased thickness, a folding wrinkle easily develops in the boundary region between the absorbent body and the flaps as stated above. Hence the present invention is effective when the absorbent body has a thickness of 3.5 mm or greater. Where the absorbent body and the flap are largely different in thickness, a folding wrinkle easily develops in the boundary region between the absorbent body and the flap as stated above. Hence the present invention is effective when the thickness difference between the absorbent body and the flap is 3.0 mm or greater, particularly 3.5 mm or greater, more particularly 5.0 mm or greater. To avoid hardening around the flaps, the embossing is preferably conducted only on the constituent material above the absorbent core, i.e., the topsheet and/or the side sheet but not on the absorbent core.

Where the materials forming the side sheets or leak guards (standing cuffs) used on the skin facing side of an absorbent article contain a reduced amount of a pigment such as titanium oxide, the sheets easily bend when bonded to the topsheet because of reduced stiffness and easily create wrinkles when folded as such. To emboss the side sheets and/or the leak guards according to the present invention is advantageous in that the wrinkles are prevented from growing. When the titanium oxide content in the side sheets and/or the leak guards is less than one-third, especially less than one-fifth, of that of the topsheet, the difference in stiffness becomes noticeable. In such cases the embossing exerts great effects in preventing large wrinkles from occurring. When, in particular, the titanium oxide content in the side sheets and/or the leak guards is 1% by weight or less, more particularly 0.8% by weight or less, the effects of the embossing are pronounced.

What is claimed is:

1. An individual package structure having an absorbent article folded and packaged in a wrapper, the absorbent article having two longitudinal side portions and comprising an absorbent body having two longitudinal side portions and a pair of flaps extending laterally outward from the longitudinal side portions of the absorbent body, the absorbent body having a topsheet that provides a skin facing side, a backsheet that provides a garment facing side, and an absorbent core between the skin facing side and the garment facing side, wherein the absorbent article has the flaps folded over the skin facing side thereof along respective two first fold lines, is folded along at least one second fold line perpendicular to the longitudinal direction of the absorbent body, and the absorbent article has a plurality of embossed patterns on and/or near the first fold lines, wherein the embossed patterns comprise at least two linear pattern units each having a larger component in the first fold line direction than in a direction perpendicular to the first fold line direction, and wherein the linear pattern units of the embossed patterns do not intersect or connect with each other, the linear pattern units are arranged along the longitudinal direction of the longitudinally extending fold line on both sides of the longitudinally extending fold line, and the embossed patterns are non-straight lines, wherein the linear pattern units of the embossed patterns are not aligned on the same level with each other in the longitudinal direction of the absorbent article but are arranged out of position to each other in the longitudinal direction of the absorbent article;

wherein the embossed pattern is formed by embossing a side sheet disposed on said longitudinal side portions of said skin facing side of said absorbent body, said side sheet having a two-layered structure by folding back on said skin facing side in the width direction of said absorbent article;

wherein said side sheet is arranged so as to extend outwardly and inwardly over a longitudinal side portion of said topsheet and said embossed pattern is formed at a position overlapped with said longitudinal side portions of said topsheet; and wherein a region of said absorbent article which is located outer to said topsheet in the widthwise direction of said absorbent article is made of an outboard extension of said backsheet and an outboard extension of said side sheet.

2. The individual package structure according to claim 1, wherein the plurality of embossed patterns include a second embossed pattern on and/or near the second fold line and in both the longitudinal side portions thereof.

3. The individual package structure according to claim 1, wherein each of the two first fold lines intersects with the second fold line.

4. The individual package structure according to claim 1, wherein the flaps are each formed of a material separate from the absorbent body.

5. The individual package structure according to claim 1, wherein the embossed patterns comprise pattern units along the first fold line direction.

6. The individual package structure according to claim 1, wherein the embossed patterns comprise at least two pattern units arranged on the both sides of the first fold line.

7. The individual package structure according to claim 1, wherein the embossed patterns comprise a pattern formed by using an embossing roll.

8. The individual package structure according to claim 1, wherein the plurality of embossed patterns are on constituent material above the absorbent core but are not on the absorbent core.

9. The individual package structure according to claim 1, wherein and the plurality of embossed patterns are on the skin facing side of the absorbent body and/or on the pair of flaps.

10. The individual package structure according to claim 8, wherein and the plurality of embossed patterns are on the skin facing side of the absorbent body and/or on the pair of flaps.

* * * * *